(12) United States Patent
Paltiel-Zucati et al.

(10) Patent No.: US 7,858,371 B2
(45) Date of Patent: Dec. 28, 2010

(54) METHOD OF SEPARATING EMBRYO SUSPENSION MASS

(75) Inventors: Judith N Paltiel-Zucati, Maple Valley, WA (US); Robert A Starr, Auburn, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 70 days.

(21) Appl. No.: 12/212,094

(22) Filed: Sep. 17, 2008

(65) Prior Publication Data

US 2009/0083884 A1    Mar. 26, 2009

Related U.S. Application Data

(60) Provisional application No. 60/975,250, filed on Sep. 26, 2007.

(51) Int. Cl.
*C12N 5/00* (2006.01)
*C12N 5/02* (2006.01)

(52) U.S. Cl. .................... 435/430; 435/410; 435/430.1

(58) Field of Classification Search .............. 435/410, 435/430, 430.1
See application file for complete search history.

(56) References Cited

U.S. PATENT DOCUMENTS 5,587,312 A * 12/1996 van Holst et al. ........... 435/421

2005/0155119 A1    7/2005   Jayakumar

FOREIGN PATENT DOCUMENTS

| EP | 0899341 | 3/1999 |
| EP | 0899341 A | 3/1999 |

OTHER PUBLICATIONS

Tsukahara et al. "Separation and analysis of cell types involved in early stages of carrot somatic embryogenesis," Plant Cell, Tissue and Organ Culture 47: 145-151, 1997.*
Fujimura et al. "Synchronization of Somatic Embryogenesis in a Carrot Cell Suspension Culture," Plant Physiol. (1979) 64, pp. 162-164.*
Dunstan D I et al "Origins and Early Growth of Celery Embryoids", New Phytologist, vol. 91, No. 1, 1982, pp. 121-128, XP002505675, ISSN: 0028-646X, Abstract p. 122.
Shohael et al: "Effect of Light on Oxidative Stress, Secondary Metabolites and Induction of Antioxidant Enzymes in *Eleutherococcus senticocosus* Somatic Embryos in Bioreactor" Process Biochemistry, Elsevier, NL, vol. 41, No. 5, May 1, 2006, pp. 1179-1185, XP005350059, ISSN: 1359-5113, Point 2.2, p. 1180.

(Continued)

*Primary Examiner*—Susan B McCormick Ewoldt
(74) *Attorney, Agent, or Firm*—Christensen O'Connor Johnson Kindness PLLC

(57) ABSTRACT

A method of separating an embryo suspension mass is provided. The method includes supplying an embryo suspension mass culture having a plurality of first particles of a first size and a plurality of second particles of a second size different at least in part from the first size of the first particles. The method also includes suspending the embryo suspension mass culture in a fluid to create a mixture and forcing the mixture through a filter while maintaining the mixture in the fluid to separate the first particles from the second particles.

9 Claims, 4 Drawing Sheets

OTHER PUBLICATIONS

Peran-Quesada R et al: "Factors Affecting Maturation of Avocodo Somatic Embryos", Scientia Horticulturae, Elsevier Science Publishers, XX, vol. 102, No. 1, Oct. 15, 2004, pp. 61-73, XP004560476, ISSN: 0304-4238, p. 62, LST Paragraph—p. 63, Paragraph 1.

Rodriguez D L et al: "Mechanical Purification of Torpedo Stage Somatic Embryos of *Daucus-carota L*", Plant Cell Tissue and Organ Culture, vol. 23, No. 1, 1990, pp. 9-14, XP008099086, ISSN: 0167-6857.

Rodriguez, D. L., et al., Mechanical purification of torpedo stage somatic embryos of *Daucus carota L*. Plant Cell Tissue and Organ Culture, 1990, vol. 23, No. 1, pp. 9 to 14.

Peran-Quesada, P., et al., Factors affecting maturation of avocado somatic embryos, Scientia Horticulturale, 2004, vol. 102, No. 1, pp. 61 to 73; cf p. 62, the last paragraph, to p. 63, the first paragraph.

Shohael, A.M., et al., Effect of light on oxidative stress, secondary metabolites and induction of antioxidant enzymes in *eleutherococcus senticcosis* somatic embryos in bioreactor, Process Biochemistry, 2006, vol. 41, No. 5, pp. 1179 to 1185; cf p. 11 80 Item 2.2.

Dunstant, D.I., et al., Origin and early growth of celery embryoids. New Phytologist, 1982, vol. 91, No. 1, pp. 121 to 128; cf. the Abstract, p. 122, paragraph Embryoid plating, p. 126, paragraph 4.

\* cited by examiner

METHOD OF SEPARATING EMBRYO SUSPENSION MASS

BACKGROUND

Asexual propagation of plants has been shown for some species to yield large numbers of genetically identical embryos, each having a capacity to develop into a normal plant. Such embryos are usually further cultured under laboratory conditions until they reach an autotrophic "seedling" state characterized by an ability to produce their own food via photosynthesis, resist desiccation, produce roots able to penetrate soil, and fend off soil microorganisms. Some researchers have experimented with the production of artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

An embryo suspension mass ("ESM") is used to cultivate embryos that are subsequently inserted into manufactured seeds. Current somatic embryogenesis involves the ongoing maintenance and planting of ESM having diverse mixtures of cell clump sizes and types. The inventors of the current disclosure have discovered that small, usually single cells from the ESM generally have a higher yield than larger cells. That is, small cells tend to have a higher rate of survival and ultimately germinate into healthy plants or trees.

Currently available methods for size separation include passively pouring cell culture onto a sieve or set of nested sieves. Another currently available method is density-based centrifugation where cell culture is disposed in a test tube with a separation media, such as Percoll or Ficoll. The test tubes are centrifuged to segregate the cells on the basis of density.

Although such methods for size separation are effective, they are not without their problems. As a non-limiting example, such methods often subject the cells to contamination. Additionally, when centrifugation is included as part of the density separation, the centrifuge often causes shearing and compaction damage to the cells.

Thus, there exists a need for a method of separating an ESM that is capable of reliably separating the ESM at a relatively low cost, and minimizing the risk of damaging or contaminating the ESM.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method of separating an embryo suspension mass is provided. The method includes supplying an embryo suspension mass culture having a plurality of first particles of a first size and a plurality of second particles of a second size different at least in part from the first size of the first particles. The method also includes suspending the embryo suspension mass culture in a fluid to create a mixture and forcing the mixture through a filter while maintaining the mixture in the fluid to separate the first particles from the second particles.

DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION

Figure 1:
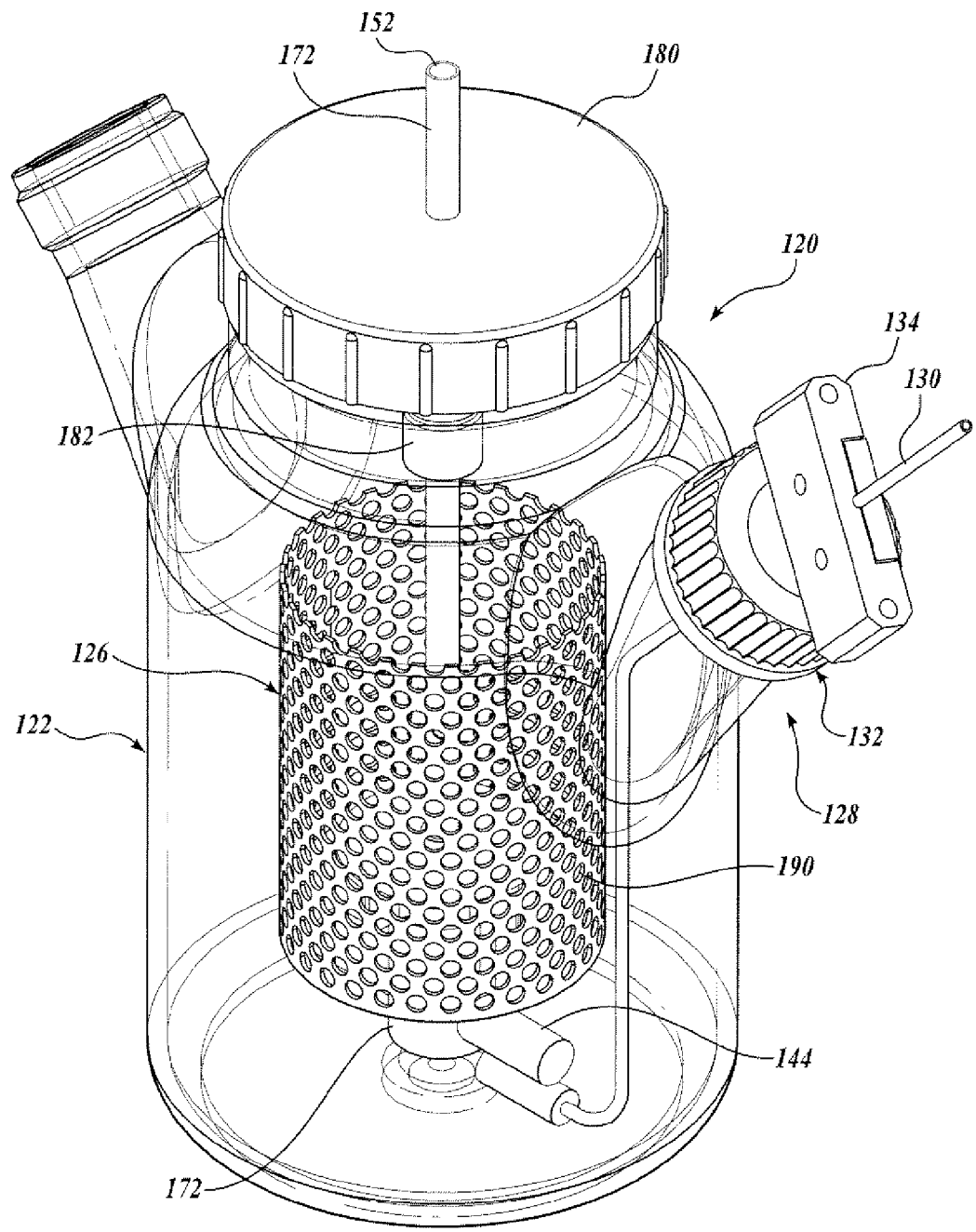
FIG. 1 is an isometric view of a filtering device constructed in accordance with one embodiment of the present disclosure.

A filtering device 120 constructed in accordance with one embodiment of the present disclosure may be best seen by referring to FIG. 1. The filtering device 120 may be suitably adapted for inclusion in an automated assembly used to cultivate embryos used in the construct of artificial seeds. Alternatively, such a filtering device 120 is suitably adapted to stand alone as a separate assembly to harvest either embryos or culture used to cultivate embryos for insertion into well-known manufactured seeds.

Figure 2:
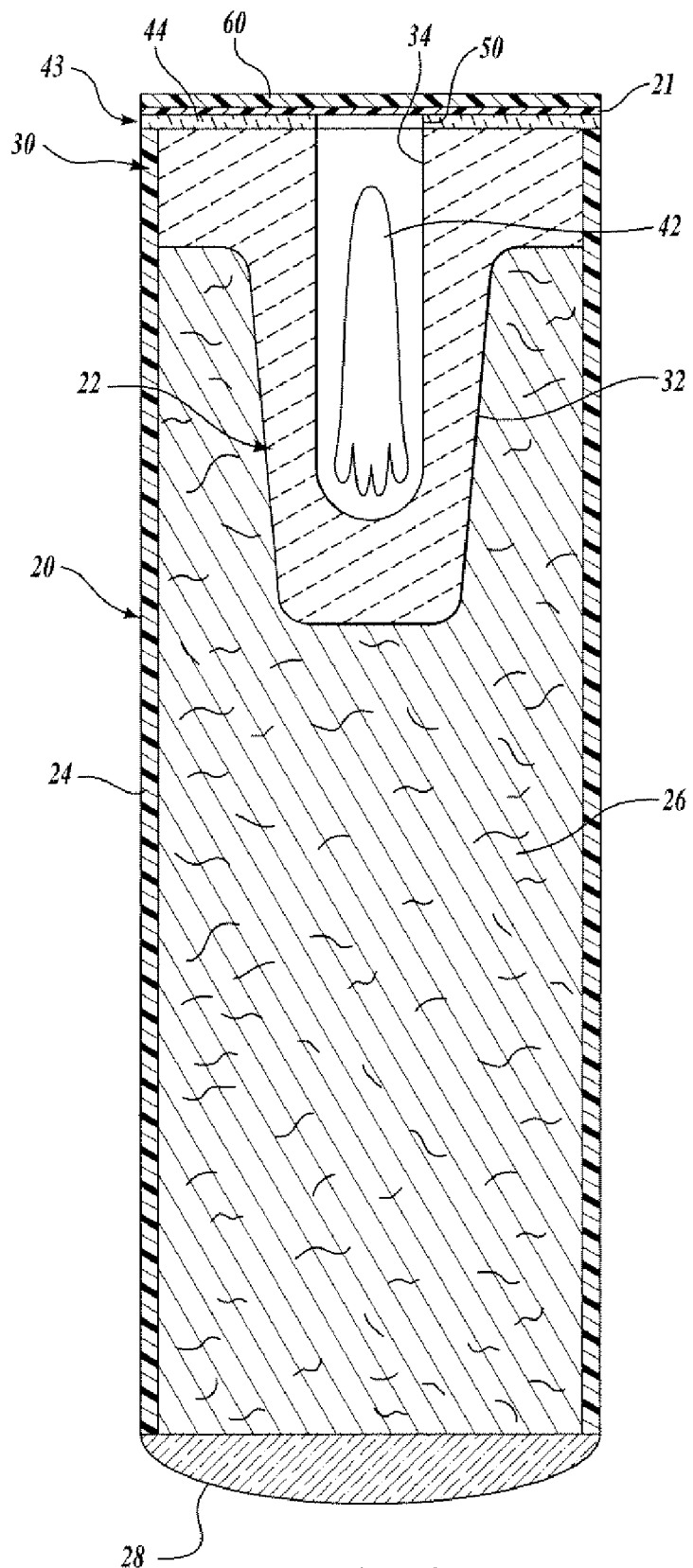
FIG. 2 is a cross-sectional side planar view of a manufactured seed.

For clarity and background, the structure of a manufactured seed 20 is described with reference to FIG. 2. The manufactured seed 20 includes a cylcap 22, a seed shell 24, nutritive media 26, such as a gametophyte, and a dead end seal 28. The seed shell 24 is suitably formed from a section of tubular material. In one embodiment, the seed shell 24 is a sectioned straw of fibrous material, such as paper. The sections of straw may be pre-treated in a suitable coating material, such as wax.

The cylcap 22, also known as a restraint, is suitably manufactured from a porous material having a hardness strong enough to resist puncture or fracture by a germinating embryo, such as a ceramic or porcelain material, and includes an end seal portion 30 and a cotyledon restraint portion 32. The cotyledon restraint portion 32 is suitably integrally or unitarily formed with the end seal portion 30. The cylcap 22 also includes a longitudinally extending cavity 34 extending through the end seal portion 30 and partially through one end of cotyledon restraint portion 32. The cavity 34 is sized to receive a plant embryo 42 therein.

In certain embodiments, as the cylcap 22 is suitably manufactured from a porous material, it may be desirable to coat the cylcap 22 with a barrier material to reduce the rate of water loss and restrict or reduce microbial entry. Such barriers include wax, polyurethane, glaze, nail polish, and a coating sold by Airproducts Airflex 4514.

The embryo 42 is disposed within the cavity 34 and is suitably sealed therein by a live end seal 43. The live end seal 43 includes a primary end seal 44 and a secondary end seal 21. The primary end seal 44 is suitably formed from a PCL material described above and includes a centrally located opening 50. The opening 50 is sized to correspond to diameter of the cavity 34 of the cylcap 22 to permit a germinating embryo 42 to pass therethrough. The primary end seal 44 is suitably attached to the end seal portion 30 by a variety of methods, including glue or heat bonding. Finally, the manufactured seed 20 includes a dead end seal 28 and may include a tertiary seal 60.

Figure 3:
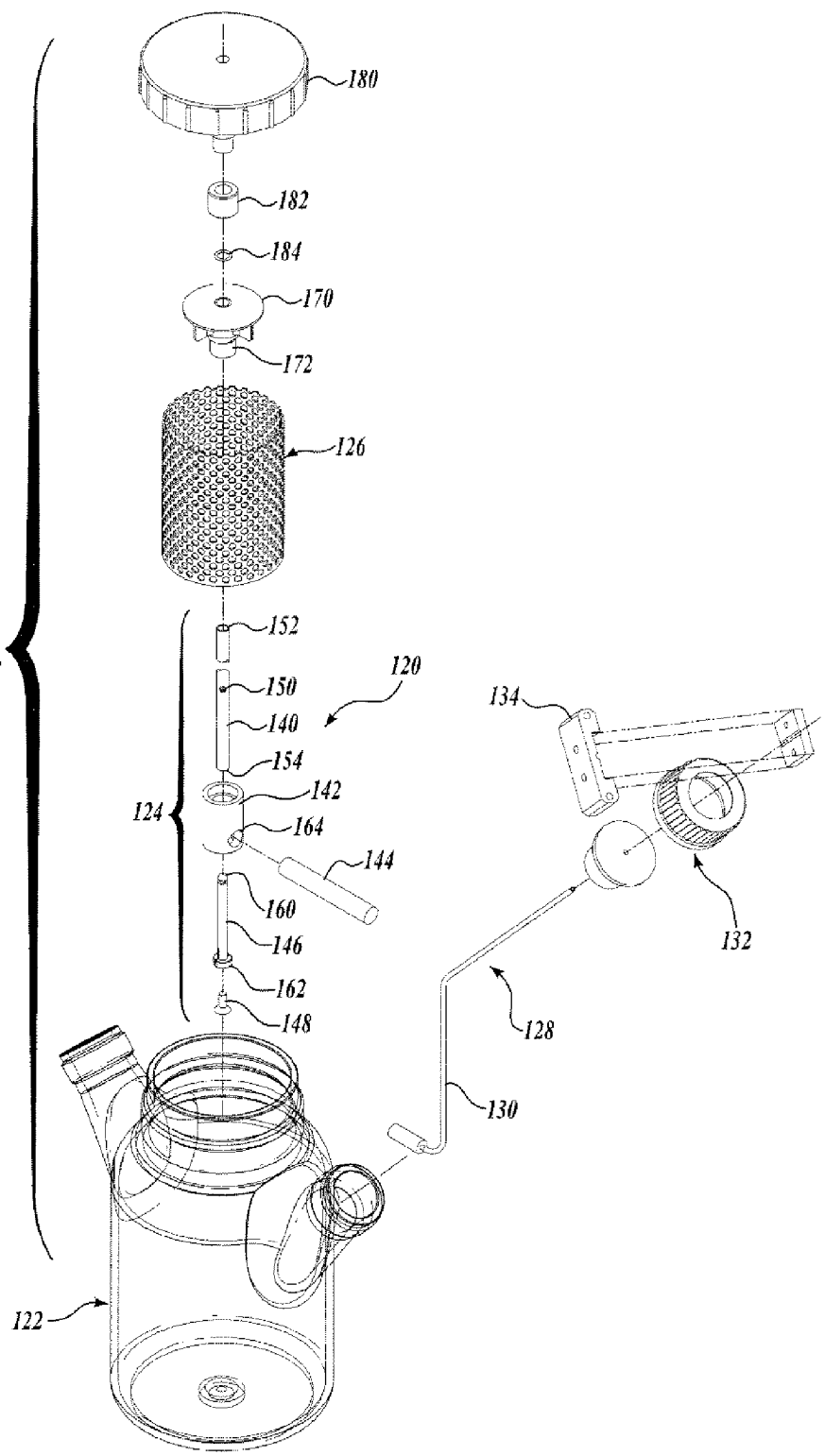
FIG. 3 is an exploded isometric view of the filtering device of FIG. 1.
Figure 4:
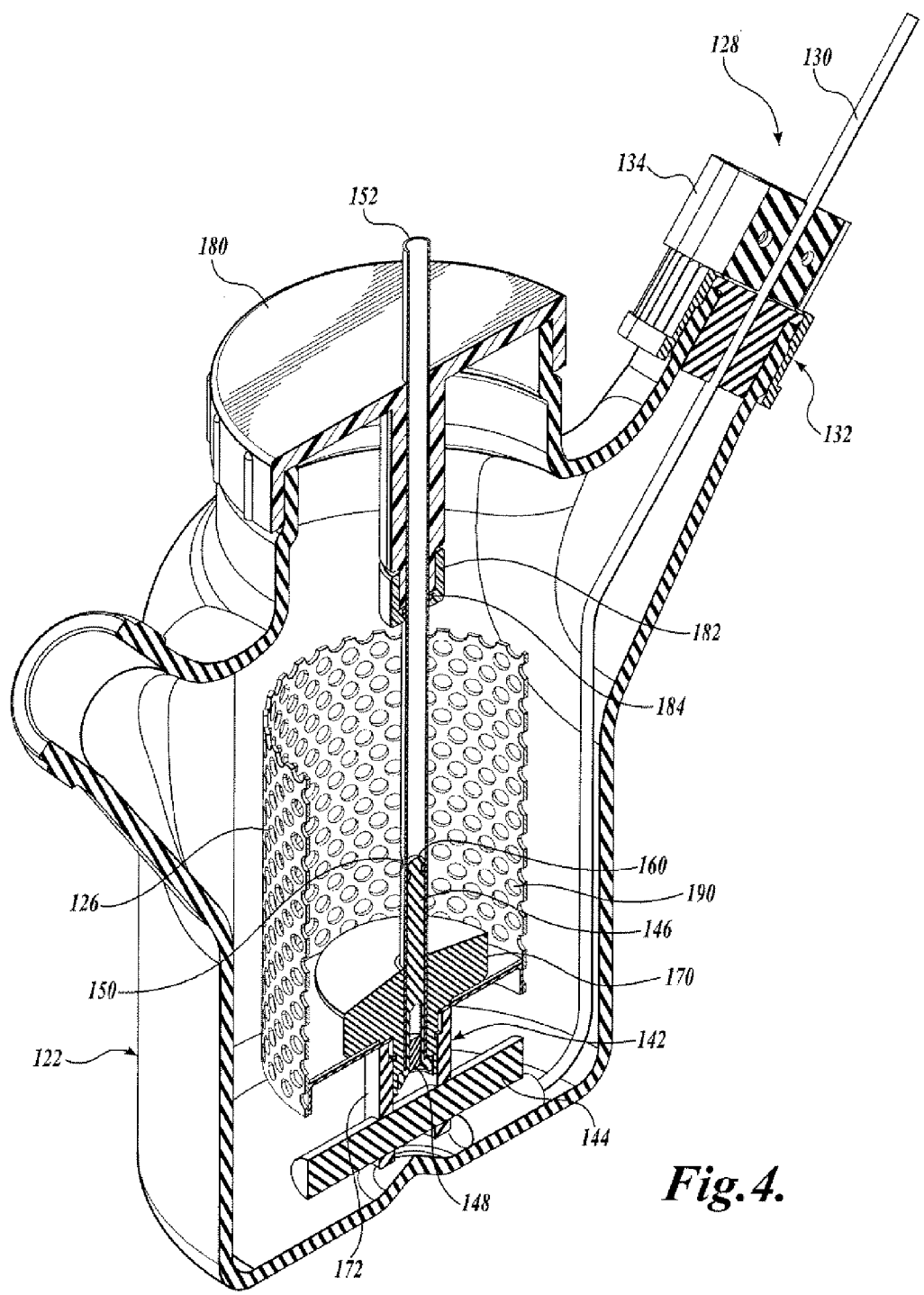
FIG. 4 is a cross-sectional isometric view of the filtering device of FIG. 1.

As may be best seen by referring to FIGS. 3 and 4, the filtering device 120 includes a beaker 122, a rotating assembly 124, and a basket 126. The beaker 122 is a well-known beaker adapted to hold a fluid (not shown). Attached to the beaker 122 is a well-known aerator 128. Such an aerator 128 includes an aeration tube 130, a cap 132, and a clamp 134. The aerator 128 is suitably disposed within the beaker 122 and, as is well known, aerates the contents of the beaker 122.

The rotating assembly 124 includes a feed tube 140, an arbor nut 142, a magnet 144, and a pin 146. The feed tube 140 is "broken" for ease of illustration and includes a supply port 150 extending through one sidewall of the tube 140. One end of the feed tube 140 defines a feed end 152, while the other end defines an anchor end 154. The anchor end 154 is sized to slidably receive the pin 146 therein.

The pin 146 is suitably a cylindrically-shaped member and includes a spherically-shaped tip 160 extending from one end of the pin 146. The other end of the pin 146 includes a shoulder 162. The tip 160 is preferably spherically-shaped to minimize damage to particulate matter, such as embryo suspension mass ("ESM"), supplied through the feed end 152 of the feed tube 140, as described in greater detail below.

After the pin 146 is inserted into the anchor end 154 of the feed tube 140, a screw 148 is inserted into a corresponding port (not shown) formed in the shoulder 162 of the pin 146. Insertion of the screw 148 into the port of the pin 146 causes that end of the pin 146 to expand within the anchor end 154 of the feed tube 140, thereby attaching the pin 146 within the feed tube 140 by compression fit. Thereafter, the magnet 144 is inserted through a channel 164 extending through one end of the arbor nut 142.

The rotating assembly 124 is attached to the basket 126 by an impeller 170. The impeller 170 includes an externally-threaded stem 172 sized to threadably engage corresponding internal threads within the arbor nut 142. As attached, the impeller 170 rotates with the rotating assembly 124 by a well-known magnetic drive assembly (not shown) suitably disposed beneath the beaker 122. The feed end 152 of the feed tube 140 extends through the basket 126 and through a beaker cap 180 and is sealed thereto by an end cap 182 and O-ring 184.

As may be best seen by referring to FIG. 4, the basket 126 includes a plurality of pores 190 sized to filter the ESM. Specifically, the ESM includes a plurality of first particles of a first size and a plurality of second particles of a second size. As is known in the art, ESM is a population of variably sized clusters and associations of single embryonal cells with suspensor cells and individual suspensor cells and cellular debris. Thus, as used within this disclosure, the term "particle" is intended to include single embryonal cells, multiple embryonal cells, suspensor cells, cellular debris, embryos, etc., and any combination thereof.

During operation of the filtering device 120, the ESM is filtered by the basket 126 to segregate the plurality of particles constituting the ESM. As an example, the pores 190 may range between a diameter of 0.25 mm-1.5 mm. As non-limiting examples, the pores 190 may be 0.5 mm, 0.75 mm, 1.00 mm, or 1.25 mm in diameter. In the non-limiting example of a basket 126 having pores 190 that measure 0.5 mm in diameter, ESM filtered through the basket 126 will permit particles having a diameter of approximately 0.5 mm and smaller to pass through the pore 190. As such, the basket 126 filters at least particles having a diameter of approximately 0.5 mm from particles having a diameter greater than 0.5 mm.

Operation of the filtering device 120 may be best understood by referring to FIGS. 1 and 4. A supply of ESM is provided to the feed tube 140 through the feed end 152. The ESM matter flows within the feed tube 140 where it exits into the basket 126 through the supply port 150. The basket 126 is disposed within the beaker 122 filled with a suspension media, such as fluid. As noted above, the flow of ESM is cushioned to limit damage to the particulate matter of the ESM by the spherical end 160.

The ESM suspended in the fluid of the beaker 122 creates a mixture that is forced through the filter or basket 126 by, in one example, centrifugal force. As the mixture is forced through the pores 190 of the basket 126, it separates a plurality of first particles of a first size from a plurality of second particles of a second size different at least in part from the first size of the first particles. As an example, if the first particles are cells of larger, more mature embryos and the second particles are smaller in size than the more mature cells, the smaller cells pass through the pores 190 if they are smaller than the diameter of the ports 190 and into the base of the beaker 122. In the example where the basket 126 is magnetically driven to induce a rotating force, the centrifugal force of the rotating basket 126 propels the second particles through the pores 190.

While illustrative embodiments have been illustrated and described, it will be appreciated that various changes can be made therein without departing from the spirit and scope of the invention. As a non-limiting example, the filtering device 120 may include a second basket or filtering layer where the second basket includes pores of a different diameter from the first basket. In such an embodiment, the filtering devices provide two layers of filtration to segregate particulates from the ESM matter into separate stages. Although two baskets are described, it should be apparent that more baskets may be included to provide as many layers of filtering as desired.

The embodiments of the invention in which an exclusive property or privilege is claimed are defined as follows:

1. A method of separating an embryo suspension mass, the method comprising:
   (a) supplying an embryo suspension mass culture having a plurality of first particles of a first size and a plurality of second particles of a second size different at least in part from the first size of the first particles;
   (b) suspending the embryo suspension mass culture in a fluid to create a mixture; and
   (c) forcing the mixture through at least a first filter while maintaining the mixture in the fluid to separate the first particles from the second particles.

2. The method of claim 1 wherein forcing the mixture through at least a first filter includes applying a centrifugal force to the mixture while maintaining the mixture in the fluid.

3. The method of claim 1, wherein suspending the embryo suspension mass culture includes depositing the embryo suspension mass culture into a basket having a plurality of pores sized to permit at least the second particles but not the first particles to pass through the plurality of pores.

4. The method of claim 3, wherein forcing the mixture through at least a first filter includes applying a rotating motion to the basket to force at least the second particles through the plurality of pores while restraining at least the first particles within the basket.

5. A method of separating an embryo suspension mass, the method comprising:
   (a) supplying an embryo suspension mass culture having a plurality of first particles of a first size and a plurality of second particles of a second size different at least in part from the first size of the first particles;
   (b) suspending the embryo suspension mass culture in a fluid to create a mixture; and
   (c) applying a rotary motion to the mixture to force the mixture through a filter to separate the first particles from the second particles.

6. The method of claim 5, wherein applying a rotary motion to the mixture includes applying a centrifugal force to a filter holding the mixture.

7. The method of claim 5, wherein the filter is a basket having a plurality of pores sized to filter at least the first particles from the second particles.

8. The method of claim 7, wherein applying a rotary motion to the mixture includes applying a centrifugal force to the basket.

9. A method of separating an embryo suspension mass, the method comprising:
   (a) supplying an embryo suspension mass culture having a plurality of first particles of a first size and a plurality of second particles of a second size different at least in part from the first size of the first particles;
   (b) depositing the embryo suspension mass culture in a basket having a plurality of pores sized to filter at least the first particles from the second particles;
   (c) suspending the basket containing the embryo suspension mass culture in a fluid to create a mixture; and
   (d) applying a rotary motion to the mixture to force the mixture through the plurality of pores of the basket to separate the first particles from the second particles.

* * * * *